(12) United States Patent
Mastroianni et al.

(10) Patent No.: US 10,143,990 B2
(45) Date of Patent: Dec. 4, 2018

(54) METHOD OF DISTRIBUTING DISCRETE POLYMER NETWORKS

(71) Applicant: LIFE TECHNOLOGIES CORPORATION, Carlsbad, CA (US)

(72) Inventors: Alexander Mastroianni, Alameda, CA (US); Scott C. Benson, Alameda, CA (US); Steven M. Menchen, Fremont, CA (US); John Scott, Edgecliff (AU)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 74 days.

(21) Appl. No.: 15/203,582

(22) Filed: Jul. 6, 2016

(65) Prior Publication Data

US 2017/0007977 A1 Jan. 12, 2017

Related U.S. Application Data

(60) Provisional application No. 62/189,417, filed on Jul. 7, 2015.

(51) Int. Cl.
| | |
|---|---|
| *B01J 19/00* | (2006.01) |
| *C12Q 1/6806* | (2018.01) |
| *C12Q 1/6837* | (2018.01) |
| *C12Q 1/6869* | (2018.01) |

(52) U.S. Cl.
CPC ........ *B01J 19/0046* (2013.01); *C12Q 1/6806* (2013.01); *C12Q 1/6837* (2013.01); *C12Q 1/6869* (2013.01); *B01J 2219/005* (2013.01); *B01J 2219/00317* (2013.01); *B01J 2219/00545* (2013.01); *B01J 2219/00648* (2013.01); *B01J 2219/00659* (2013.01); *B01J 2219/00677* (2013.01); *B01J 2219/00722* (2013.01)

(58) Field of Classification Search
CPC ...... B01J 19/0046; C12Q 1/6806; C12Q 1/68; C12Q 1/6837
See application file for complete search history.

(56) References Cited

U.S. PATENT DOCUMENTS

2001/0029049 A1* 10/2001 Walt .................. G01N 21/6428
436/518
2013/0210991 A1* 8/2013 Fonnum ................... C08F 6/24
524/547

FOREIGN PATENT DOCUMENTS

| WO | WO-2014/013263 | 1/2014 |
| WO | WO-2014/160962 | 10/2014 |
| WO | WO-2015/038954 | 3/2015 |
| WO | WO-2017/007838 | 1/2017 |

OTHER PUBLICATIONS

Ye et al, Aptamer-based suspension array indexed by structural color and shape, 2011, J. Mater. Chem., 2011, 21, 18659-18664 (Year: 2011).*

(Continued)

*Primary Examiner* — Narayan K Bhat (57) ABSTRACT

A method of preparing a discrete polymer network array include mixing a plurality of nucleic acid polymer networks with a plurality of color-activated polymer networks to form a dispersion, applying the dispersion to an array of wells, the nucleic acid polymer networks selectively depositing into wells of the array of wells, and rinsing the array of wells to selectively remove the plurality of color-activated polymer networks.

18 Claims, 7 Drawing Sheets

(56) References Cited

OTHER PUBLICATIONS

Lim, et al., "Correlated matrix-assisted laser desorption/ionization mass spectrometry and fluorescent imaging of photocleavable peptide-coded random bead-arrays" *Rapid Communications in Mass Sepctrometry*, vol. 28, No. 1, Nov. 21, 2013, 49-62.
Meiring, et al., "Hydrogel Biosensor Array Platform Indexed by Shape", *Chemical Material*, vol. 16, No. 26, Dec. 1, 2004, 5574-5580
PCT/US2016/041171, International Search Report and Written Opinion, dated Sep. 21, 2016, 1-12.
PCT/US2016/041171, International Preliminary Report on Patentability, dated Jan. 18, 2018, 1-8.

* cited by examiner

METHOD OF DISTRIBUTING DISCRETE POLYMER NETWORKS

CROSS-REFERENCE TO RELATED APPLICATION(S)

This application claims benefit of U.S. Provisional Application No. 62/189,417, filed Jul. 7, 2015, which is incorporated herein by reference in its entirety.

FIELD OF THE DISCLOSURE

This disclosure, in general, relates to methods of distributing discrete polymer networks, for example, loading a genetic testing device and further to those systems and apparatuses for performing such methods.

BACKGROUND

Genetic testing is of increasing interest to the medical and scientific communities. In medicine, genetic testing provides details regarding the origin of disease, susceptibility to ailments, responsiveness to drugs, and identification of inherited traits. Animal sciences look to genetic testing to provide similar details in addition to using genetic testing for classification of species and determining migration patterns, among other uses. In other fields, such as agricultural science, genetic testing is used to identify gene sequences that can be incorporate into strains of flora or fauna to reduce susceptibility to pests and disease and to improve production.

While many genetic testing techniques have been proposed, recent genetic testing techniques rely on nucleic acid conjugated polymer networks disposed on a substrate, such as a substrate of an optical device or an ion sensitive device that can be used to detect nucleotide incorporation, for example. In a particular example, conjugated discrete polymer networks can be deposited into wells disposed over ion sensitive field effect transistors, which measure pyrophosphate or hydrogen ions released as a result of nucleotide incorporation. Other techniques rely on arrays of discrete polymer networks disposed on substrates without wells.

SUMMARY

In a first aspect, a method of preparing a discrete polymer network array includes mixing a plurality of nucleic acid polymer networks with a plurality of color-activated polymer networks to form a dispersion, applying the dispersion to an array of wells, the nucleic acid polymer networks selectively depositing into wells of the array of wells, and rinsing the array of wells to selectively remove the plurality of color-activated polymer networks.

In a second aspect, a method of forming a color-activated polymer network includes preparing hydrogel polymer network to include halide or amine terminal groups, reacting the hydrogel polymer network with a dye having amine, hydrizide, or N-hydroxysuccinimide functionality, and rinsing excess dye from the hydrogel polymer network.

In a third aspect, a discrete polymer network includes a hydrogel polymer network and a dye covalently coupled to the hydrogel polymer network. In an example of the third aspect, the hydrogel polymer network includes an acrylamide, a polyethylene glycol, a copolymer thereof, or a combination thereof. For example, the acrylamide includes a hydro alkylacrylamide monomer.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, a method for performing a genetic test includes mixing color-active polymer networks with nucleic acid polymer networks to form a dispersion. The dispersion is applied to an array of wells. The nucleic acid polymer networks are selectively deposit into the array of wells, while the color-active polymer networks remain in the dispersion. The color-active polymer networks are rinsed from the array of wells and the nucleic acid polymer networks selectively remain in the wells of the array of wells. The method can further include applying reagents and nucleotides. When the nucleotides are incorporated to form strands complementary to target nucleic acids on the nucleic acid polymer networks, a signal is produced in the genetic testing device. The signal is indicative of nucleotide incorporation and can be used to sequence the target nucleic acids. In an example, the nucleic acid polymer networks and the color-active polymer networks can be formed of a similar polymer. Further, the nucleic acid polymer networks and the color-active polymer networks can be of similar size. In particular, the nucleic acid polymer networks or the color-active polymer networks have a size that is less than the effective diameter of a well of the array of wells. The color-active polymer networks can be free of conjugated nucleic acids.

The color-active polymer networks can be formed by conjugating a dye to a polymer matrix. For example, a hydrogel discrete polymer network can be prepared to include a hydroxyl, carboxyl, halide, or amine terminal group. The hydroxyl, carboxyl, amine, or halide terminal group can be reacted with a dye having an amine, hydrizide or N-hydroxysuccinimide functionality. Excess dye can be rinsed from the color-active polymer networks. The starting polymer of the color-active polymer networks can be similar to that of the nucleic acid polymer networks. In addition, the nucleic acid polymer network prior to conjugation with the nucleic acid and the hydrogel discrete polymer network used to form the color-active polymer network can have similar size prior to conjugation.

Figures 1, 5:
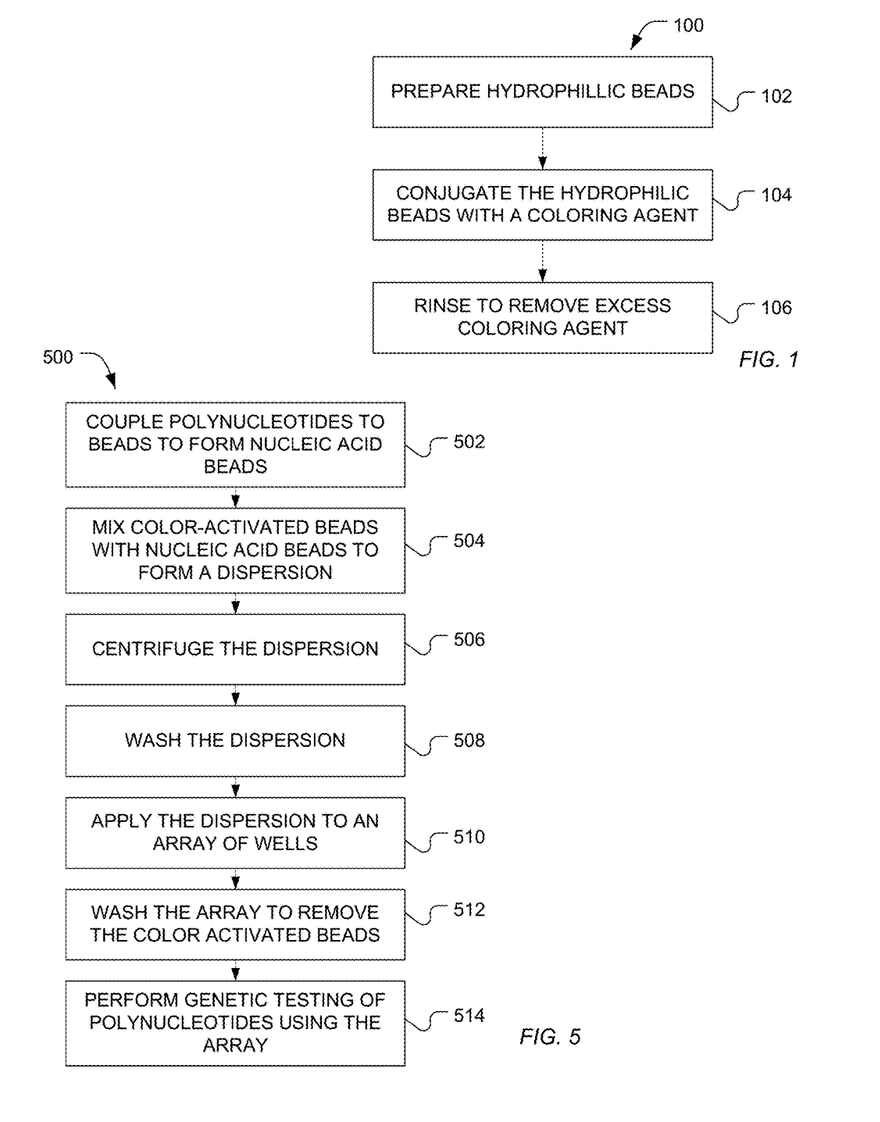
FIG. 1 includes a flow diagram of an exemplary method for forming color-active polymer networks.
FIG. 5 includes a flow diagram of an exemplary method for performing a genetic test.

FIG. 1 includes an illustration of an exemplary method 100 for preparing a color-active polymer network. As illustrated at 102, a hydrophilic discrete polymer network can be prepared. For example, the hydrophilic discrete polymer network can be a hydrogel discrete polymer network. In a particular example, the hydrophilic discrete polymer network includes functionality that can be used to conjugated a coloring agent. For example, the hydrophilic discrete polymer network can include a hydroxyl functional group, a halide functional group, a carboxyl functional group, an amine functional group, or a combination thereof.

The hydrophilic discrete polymer networks can be formed of hydrophilic polymers. The monomer forming the polymer can be a radically polymerizable monomer, such as a vinyl-based monomer. In particular, the monomer can include a hydrophilic monomer. In an example, the hydrophilic monomer can include acrylamide, vinyl acetate, hydroxyalkylmethacrylate, or any combination thereof. In a particular example, the hydrophilic monomer is an acrylamide, such as an acrylamide including hydroxyl groups, amino groups, carboxyl groups, or a combination thereof. In an example, the hydrophilic monomer is an aminoalkyl acrylamide, an acrylamide functionalized with an amine terminated polypropylene glycol, an acrylopiperazine, or a combination thereof. In another example, the acrylamide can be a hydroxyalkyl acrylamide, such as hydroxyethyl acrylamide. In particular, the hydroxyalkyl acrylamide can include N-tris (hydroxymethyl)methyl)acrylamide, N-(hydroxymethyl) acrylamide, or a combination thereof. In a further example, a mixture of monomers, such as a mixture of hydroxyalky acrylamide and amine functionalize acrylamide or a mixture of acrylamide and amine functionalized acrylamide, can be used. In an example, the amine functionalize acrylamide can be included in a ratio of hydroxyalkyl acrylamide: amine functionalized acrylamide or acrylamide: amine functionalized acrylamide in a range of 100:1 to 1:1, such as a range of 100:1 to 2:1, a range of 50:1 to 3:1, a range of 50:1 to 5:1 or even a range of 50:1 to 10:1.

In another example, the monomer can include a carboxyl coupling site and, for example, can have the formula:

wherein $R_1$ is an alkyl group having between 3 and 10 carbons, is a polyether group having between 1 and 10 ether units, or is another non-ionic polar group, wherein $R_2$ is hydrogen, a linear or branched alkyl group having between 3 and 8 carbons or is a silyl group, and wherein $R_3$ is hydrogen or an alkyl group having between 1 and 6 carbons. In a particular example, $R_1$ is an alkyl group having between 3 and 10 carbons or is a polyether group having between 1 and 10 ether units. For example, $R_1$ can be an alkyl group having 3 to 6 carbons, such as 3 to 5 carbons. In another example, $R_1$ can be a polyether group including units, such as including ethylene oxide or propylene oxide units, in a range of 2 to 6 units, such as 2 to 4 units. In a further example, R1 can be a non-ionic polar group, for example, including an amide. In an example, $R_2$ is a branched alkyl group, for example, having 3 to 5 carbons, such as 4 carbons. In particular, $R_2$ can be an isopropyl, isobutyl, sec-butyl, or tert-butyl group, or any combination thereof. The silyl group can be a trialkyl silyl group, an organo disilyl group, or an organo trisilyl group. For example, the trialkyl silyl group can be a trimethyl silyl or a triethyl silyl group. In a particular example, $R_2$ is hydrogen. In a further example, $R_3$ is hydrogen. In another example, $R_3$ is a methyl or ethyl group.

In a particular example, the hydrophilic monomer includes hydroxyl groups or includes amines In another example, the hydrophilic monomer includes carboxy groups.

The polymer of the discrete polymer network can also include a crosslinker. In an example, the crosslinker is included in a mass ratio of monomer to crosslinker in a range of 15:1 to 1:2, such as a range of 10:1 to 1:1, a range of 6:1 to 1:1, or even a range of 4:1 to 1:1. In particular, the crosslinker can be a divinyl crosslinker. For example, a divinyl crosslinker can include a diacrylamide, such as N,N'-(ethane-1,2-diyl)bis(2-hydroxy ethyl)acrylamide, N,N'-(2-hydroxypropane-1,3-diyl)diacrylamide, or a combination thereof. In another example, a divinyl crosslinker includes ethyleneglycol dimethacrylate, divinylbenzene, hexamethylene bisacrylamide, trimethylolpropane trimethacrylate, a derivative thereof, or a combination thereof.

The hydrophilic polymer discrete polymer network formed from the above monomers and optionally crosslinker can include hydroxyl or amine terminal groups. Hydroxyl groups can be converted to halide or amine groups through nucleophilic substitution. For example, hydroxyl groups on the hydrophilic discrete polymer network can be activated by replacing at least a portion of the hydroxyl groups with a chlorine group. Exemplary reagents to facilitate substitution can be derived from tresyl, mesyl, tosyl, or fosyl chloride, or any combination thereof. In another example, amine groups on the hydrophilic polymer can be activated.

Returning to FIG. 1, the hydrophilic discrete polymer networks can be conjugated with a coloring agent. In a particular example, the hydrophilic discrete polymer network can be halogenated. For example, application of tresyl, mesyl, tosyl, or fosyl chloride can halogenate hydroxyl groups of the discrete polymer networks. The halogen functionality can be reacted with amine functionality of a dye molecule, resulting in conjugation of the dye to the discrete polymer network. Alternatively, the halogen functionality can be reacted to form amine functionality or monomers can be selected to give the discrete polymer network amine functionality, which can be conjugated to a dye using succinimide conjugation or isocyanate conjugation.

Other activation chemistries include incorporating multiple steps to convert a specified functional group to accommodate specific desired linkages. For example, the sulfonate modified hydroxyl group can be converted into a nucleophilic group through several methods. In an example, reaction of the sulfonate with azide anion yields an azide substituted hydrophilic polymer. The azide can be used directly to conjugate to an acetylene substituted biomolecule via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted biomolecule to yield a urea linkage between the linker and the biomolecule. In another example, using bis-NHS esters yields an amide linkage between the polymer and the linker and a residual NHS ester group that is capable of reacting with an amino substituted biomolecule to yield an amide linkage between the linker and the biomolecule. In a further example, using cyanuric chloride yields an amino-triazine linkage between the polymer and the linker and two residual chloro-triazine groups one of which is capable of reacting with an amino substituted biomolecule to yield an amino-triazine linkage between the linker and the biomolecule. Other nucleophilic groups can be incorporated into the polymer network via sulfonate activation. For example, reaction of sulfonated particles with thiobenzoic acid anion and hydrolysis of the consequent thiobenzoate incorporates a thiol into the polymer network which can be subsequently reacted with a maleimide substituted biomolecule to yield a thio-succinimide linkage to the biomolecule. Thiol can also be reacted with a bromo-acetyl group.

In an example in which the polymer network include carboxyl coupling sites, a carboxyl activating compound, such as a succinimidyl compound, can be applied to the polymer substrate, for example in a non-aqueous solvent. The succinimidyl compound can react with the carboxyl functionality, such as an alkanoic acid moiety or ester derivative thereof, to form a succinimidyl alkanoate moiety, referred to herein as activation. A succinimidyl compound can be applied to the polymer substrate. The succinimidyl compound, for example, can be a succinimidyl uronium compound or a succinimidyl phosphonium compound. In a particular example, the succinimidyl compound is a succinimidyl uronium compound. The succinimidyl uronium compound can be an O-type succinimidyl uronium. In an example, the O-type succinimidyl uronium is an N-hydroxy succinimidyl uronium. In another example, the succinimidyl compound is a succinimidyl phosphonium compound. For example, an N-hydroxy succinimidyl compound (NHS-compound) can react with the carboxyl functionality on the substrate, for example, in a non-aqueous solvent, to form the succinimidyl alkanoate compound (C(O)NHS). The modified polymer substrate can be conjugated to a biomolecule, such as a dye modified oligonucleotide or nucleic acid, by applying an amine-terminated biomolecule, for example, dissolved in a non-aqueous solvent, to the polymer substrate.

Figure 2:
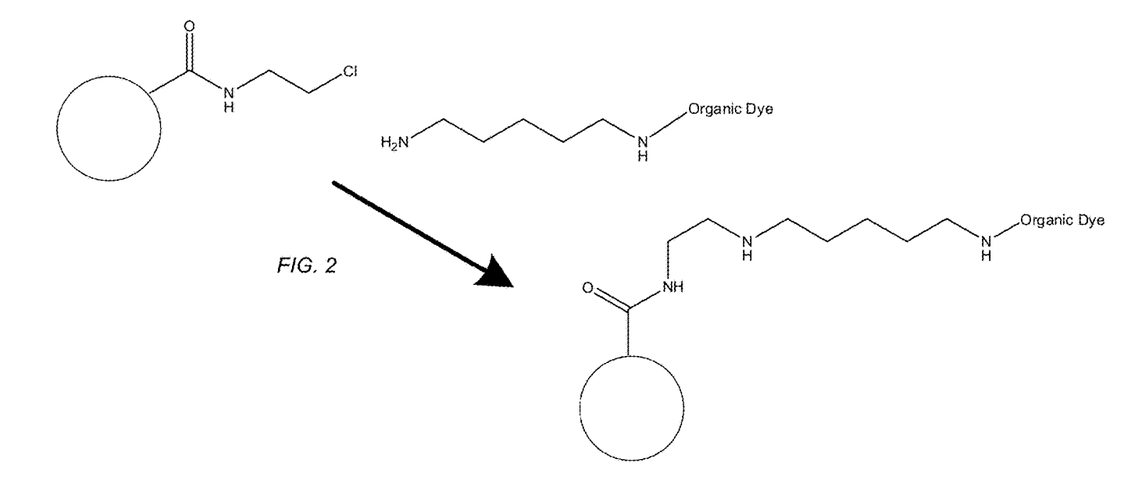
FIG. 2, FIG. 3, and FIG. 4 include illustrations of exemplary conjugation methods.
Figure 3:
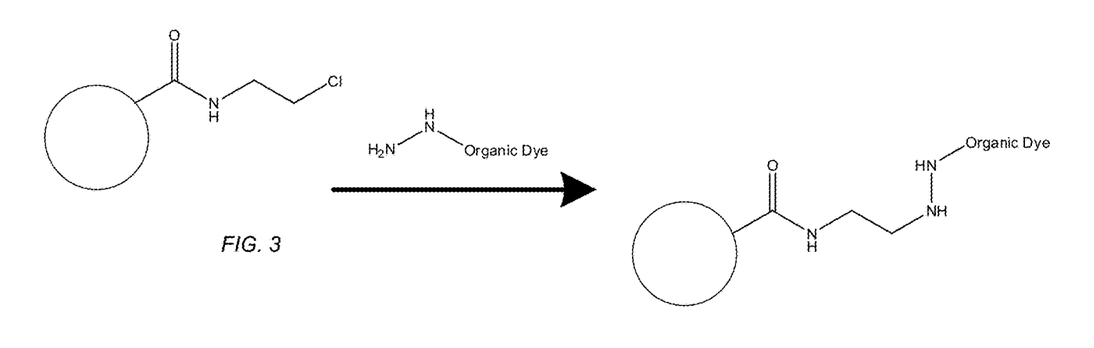

In an example illustrated in FIG. 2, a halide functional discrete polymer network, for example, derived from a polymer network including hydroxyl or amine functionality, can be reacted with an amine functional organic dye. As a result, the amine functional organic dye is covalently bonded in place of the halide functionality of the discrete polymer network. In an example illustrated in FIG. 3, a halide functional discrete polymer network can be reacted with a hydrazide functional organic dye. As a result, the hydrazide functionality replaces the halide functionality to covalently bond the organic dye to the discrete polymer network. While the discrete polymer networks of the FIG. 2 and FIG. 3 are illustrated as having a single functional group, the discrete polymer networks can have many functional groups. The functional groups can be of the same type or can be of different types. As such, following reaction with conjugated functionalized organic dyes, the discrete polymer network can optionally be conjugated to many organic dye molecules.

Figure 4:
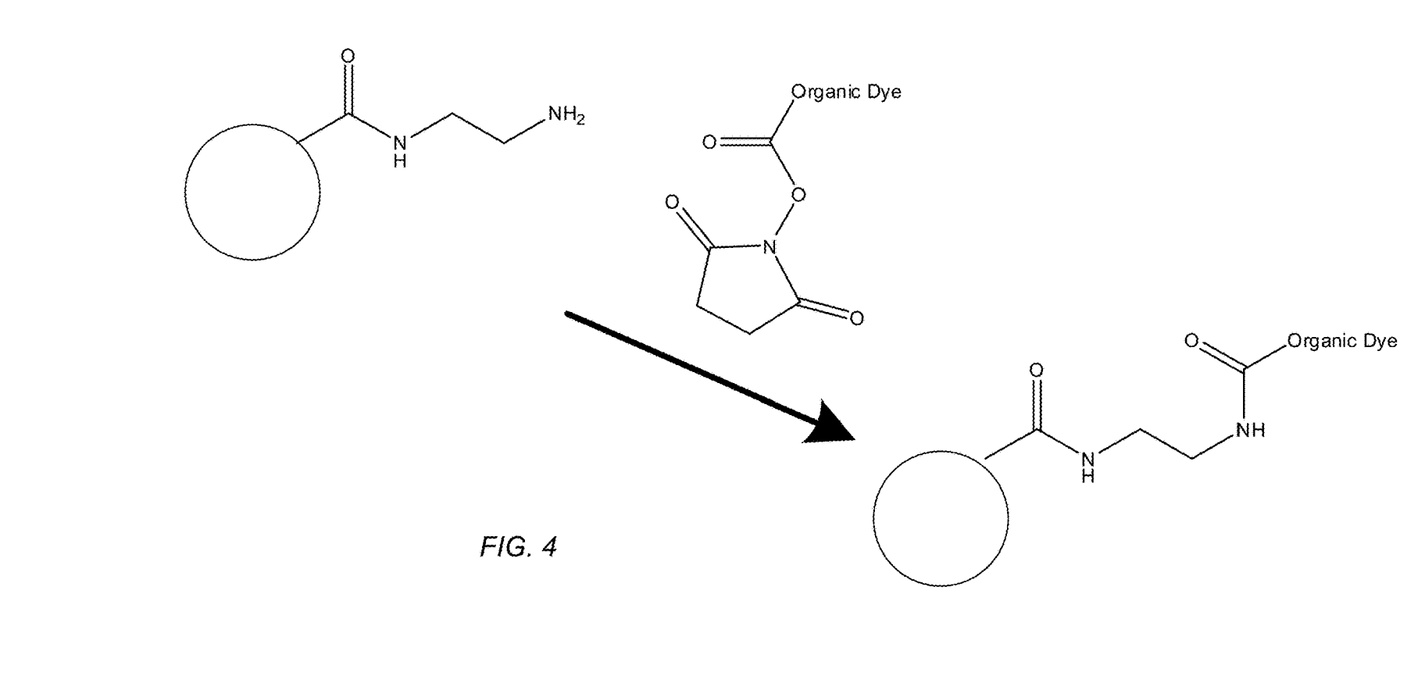

In a further example, the prepared hydrophilic discrete polymer network can include amine functionality. In an example, the amine functionality can be incorporated into the polymeric structure of the discrete polymer network. Alternatively, a halide functional discrete polymer network can be further converted to an amine functional discrete polymer network using reaction with an azide. In an example illustrated in FIG. 4, an amine functionalized discrete polymer network can be reacted with an organic dye functionalized with N-hydroxysuccinimide As such, the organic dye can be covalently bonded to the amine functional discrete polymer network.

In a particular example, the coloring agent is an organic dye, which can include coumarin, rhodamine, xanthene (such as fluorescein), cyanine dyes, derivatives thereof, or combinations thereof. In an example, the dye can be a sulfonated derivative of coumarin, rhodamine, xanthene (such as fluorescein), cyanine dyes, or a combination thereof. In particular, the dye can be hydrophilic and have a charge, such as a positive charge or a negative charge. In an example, the dye is negatively charged.

Returning to FIG. 1, excess coloring agent (e.g., organic dye) is rinsed from the discrete polymer network. For example, excess coloring agent can be rinsed from the discrete polymer network through a series of centrifuge and washing steps using water or other solvents compatible with the functionalized organic dye. The dye functionalized polymer network can be free of conjugated nucleic acids.

In a particular example, the color-active polymer networks formed through a process, such as the process of FIG. 1, can be used to load a genetic testing device and perform genetic testing. For example, FIG. 5 illustrates a method 500 that includes coupling polynucleotides to discrete polymer networks to form nucleic acid polymer networks, as illustrated at 502.

Figure 6:
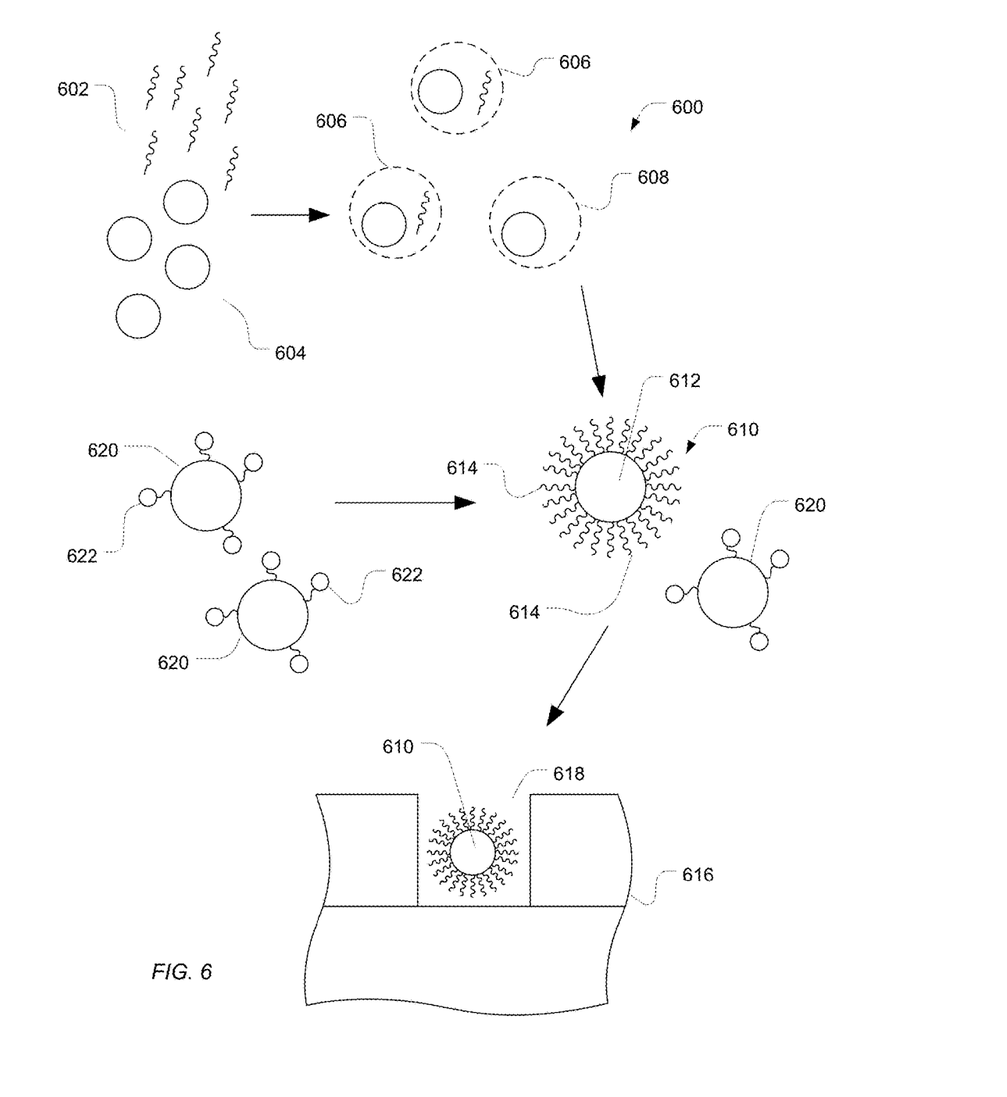
FIG. 6 includes an illustration of an exemplary method for loading an exemplary testing device.

As illustrated in FIG. 6, a plurality of discrete polymer networks 604 can be placed in a solution along with a plurality of polynucleotides 602. The plurality of discrete polymer networks 604 can be activated or otherwise prepared to bind with the polynucleotides 602. For example, the discrete polymer networks 604 can include an oligonucleotide complementary to a portion of a polynucleotide of the plurality of polynucleotides 602. In another example, the discrete polymer networks 604 can be modified with target polynucleotides 604 using techniques such as biotin-streptavidin binding.

In a particular embodiment, the hydrophilic discrete polymer networks and polynucleotides are subjected to polymerase chain reaction (PCR) amplification. Alternatively, the hydrophilic discrete polymer networks and polynucleotides are subjected to recombinase polymerase amplification (RPA), such as isothermal RPA. Such amplification reactions can be performed in an emulsion. For example, dispersed phase droplets 606 or 608 are formed as part of an emulsion and can include a hydrophilic discrete polymer network or a polynucleotide. In an example, the polynucleotides 602 and the hydrophilic discrete polymer networks 604 are provided in low concentrations and ratios relative to each other such that a single polynucleotide 602 is likely to reside within the same dispersed phase droplets as a single hydrophilic discrete polymer network 604. Other droplets, such as a droplet 608, can include a single hydrophilic discrete polymer network and no polynucleotide. Each droplet 606 or 608 can include enzymes, nucleotides, salts or other components sufficient to facilitate duplication of the polynucleotide.

In a particular embodiment, an enzyme such as a polymerase is present, bound to, or is in close proximity to the hydrophilic discrete polymer network, such as a hydrogel discrete polymer network, of the dispersed phase droplet. In an example, a polymerase is present in the dispersed phase droplet to facilitate duplication of the polynucleotide. A variety of nucleic acid polymerases can be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

In embodiments, duplication of the polynucleotide can include modulating the duplication conditions. Modulating can optionally include: increasing or decreasing the polymerase concentration; increasing or decreasing the nucleotide concentration; increasing or decreasing a cation concentration; increasing or decreasing a reaction temperature, time or pH, or the like. The modulating can include increasing or decreasing the rate of the reaction, increasing or decreasing the yield of product of the reaction, or the like. In embodiments, duplication can be performed in the presence of appropriate buffers or nucleotides (including nucleotide analogs or biotinylated nucleotides).

In particular, the polynucleotide to be amplified can be captured by the discrete polymer network. Exemplary methods for capturing nucleic acid can include hybridizing a polynucleotide to an oligonucleotide that is attached to a discrete polymer network. In embodiments, methods for capturing nucleic acids comprise: (a) providing a discrete polymer network attached to a single-stranded oligonucleotide (e.g., a capture oligonucleotide); (b) providing a single-stranded polynucleotide; and (c) hybridizing the single-stranded oligonucleotide to the single-stranded polynucleotides, thereby capturing the single-stranded polynucleotide to the discrete polymer network. In embodiments, each of the discrete polymer networks can be attached with a plurality of single-stranded oligonucleotides (e.g., capture oligonucleotides). In embodiments, step (c) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide.

In an example, the method further includes amplifying the polynucleotide into a plurality of polynucleotides and attaching at least a portion of the plurality of polynucleotides to the hydrophilic discrete polymer network, thereby generating a hydrophilic discrete polymer network including a plurality of attached polynucleotides. Alternatively, the method can further include amplifying the polynucleotide into a plurality of complementary polynucleotides by extending the oligonucleotide, thereby generating a hydrogel discrete polymer network including a plurality of attached polynucleotides.

In embodiments, methods for nucleotide incorporation comprise: conducting a nucleotide polymerization reaction on a polynucleotide that is hybridized to an oligonucleotide that is attached to a discrete polymer network. In embodiments, methods for nucleotide incorporation comprise: (a) providing a discrete polymer network attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby conducting nucleotide incorporation. In embodiments, each of the discrete polymer networks can be attached with a plurality of single-stranded oligonucleotides (e.g., capture oligonucleotides). In embodiments, steps (b), (c) or (d) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, a system comprises a single-stranded polynucleotide hybridized to a single-stranded oligonucleotide which is attached to a discrete polymer network, wherein at least one nucleotide is polymerized onto the end of the single-stranded oligonucleotide.

In embodiments, methods for primer extension comprise: conducting a primer extension reaction on a polynucleotide that is hybridized to an oligonucleotide that is attached to a discrete polymer network. In embodiments, methods for nucleic acid primer extension comprise: (a) providing a discrete polymer network attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby extending the primer. In embodiments, each of the discrete polymer networks can be attached with a plurality of single-stranded oligonucleotides (e.g., capture oligonucleotides). In embodiments, step (b), (c) or (d) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, a system comprises a single-stranded polynucleotide hybridized to a single-stranded oligonucleotide which is attached to a discrete polymer network, wherein the single-stranded oligonucleotide is extended with one or more nucleotides.

In embodiments, methods for nucleic acid amplification comprise: conducting a primer extension reaction on a polynucleotide that is hybridized to an oligonucleotide which is attached to a discrete polymer network. In embodiments, methods for nucleic acid amplification comprise: (a) providing a discrete polymer network attached to a single-stranded oligonucleotide (e.g., a primer oligonucleotide); (b) providing a single-stranded template polynucleotide; (c) hybridizing the single-stranded oligonucleotide to the single-stranded template polynucleotide; (d) contacting the single-stranded template polynucleotide with a polymerase and at least one nucleotide under conditions suitable for the polymerase to catalyze polymerization of at least one nucleotide onto the single-stranded oligonucleotide so as to generate an extended single-stranded oligonucleotide. In embodiments, the method further comprises: (e) removing (e.g., denaturing) the single-stranded template polynucleotide from the extended single-stranded oligonucleotide so that the single-stranded oligonucleotide remains attached to the discrete polymer network; (f) hybridizing the remaining single-stranded oligonucleotide to a second single-stranded template polynucleotide; and (g) contacting the second single-stranded template polynucleotide with a second polymerase and a second at least one nucleotide, under conditions suitable for the second polymerase to catalyze polymerization of the second at least one nucleotide onto the single-stranded oligonucleotide so as to generate a subsequent extended single-stranded oligonucleotide. In embodiments, steps (e), (f) and (g) can be repeated at least once. In embodiments, the polymerase and the second polymerase comprise a thermostable polymerase. In embodiments, the conditions suitable for nucleotide polymerization include conducting the nucleotide polymerization steps (e.g., steps (d) or (g)) at an elevated temperature. In embodiments, the conditions suitable for nucleotide polymerization include conducting the nucleotide polymerization step (e.g., steps (d) or (g)) at alternating temperatures (e.g., an elevated temperature and a relatively lower temperature). In embodiments, the alternating temperature ranges from 60-95° C. In embodiments, the temperature cycles can be about 10 seconds to about 5 minutes, or about 10 minutes, or about 15 minutes, or longer. In embodiments, methods for nucleic acid amplification can generate one or more discrete polymer networks each attached to a plurality of template polynucleotides comprising sequences that are complementary to the single-stranded template polynucleotide or to the second single-stranded template polynucleotide. In embodiments, each of the discrete polymer networks can be attached with a plurality of single-stranded oligonucleotides (e.g., capture oligonucleotides). In embodiments, step (b), (c), (d), (e), (f) or (g) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, methods for nucleic acid amplification (as described above) can be conducted in an aqueous phase solution in an oil phase (e.g., dispersed phase droplet).

Following PCR or RPA, nucleic acid polymer networks are formed, such as nucleic acid polymer networks 610, which can include the hydrophilic discrete polymer network 612 and a plurality of copies 614 of the polynucleotide. While the polynucleotides 614 are illustrated as being on a surface of the discrete polymer network 610, the polynucleotides can extend within the discrete polymer network 610. Hydrogel and hydrophilic discrete polymer networks having a low concentration of polymer relative to water can include polynucleotide segments on the interior of and throughout the discrete polymer network 610 or polynucleotides can reside in pores and other openings. In particular, the discrete polymer network 610 can permit diffusion of enzymes, nucleotides, primers and reaction products used to monitor the reaction. A high number of polynucleotides per discrete polymer network produces a better signal.

In embodiments, discrete polymer networks undergo an emulsion-breaking procedure and can be collected and washed in preparation for sequencing. Collection can be conducted by contacting biotin moieties (e.g., linked to amplified polynucleotide templates which are attached to the discrete polymer networks) with avidin moieties, and separation away from discrete polymer networks lacking biotinylated templates. Collected discrete polymer networks that carry double-stranded template polynucleotides can be denatured to yield single-stranded template polynucleotides for sequencing. Denaturation steps can include treatment with base (e.g., NaOH), formamide, or pyrrolidone.

Returning to FIG. 5, the color-active polymer networks can be mixed with the nucleic acid polymer networks to form a dispersion, as illustrated at 504. For example, the color-active polymer networks 620 illustrated in FIG. 6 are mixed with the nucleic acid polymer networks 612. The color-active polymer networks are conjugated to coloring agent 622, such as a dye. In another example, color-active polymer networks can be mixed with the discrete polymer networks 604 prior to amplification and optionally, again following amplification or after an enrichment process. The color-active polymer networks can be free of conjugated nucleic acids.

The color-active polymer networks can be mixed with the nucleic acid polymer networks in an amount in a range of 0.5% to 25% of the total number of nucleic acid polymer networks. For example, the amount can be in a range of 1% to 20%, such as a range of 1% to 15%, a range of 1% to 9%, or even a range of 2% to 6%.

Optionally, the dispersion can be rinsed. For example, as illustrated at 506, the dispersion can be centrifuged to drive the color-active polymer networks and the nucleic acid polymer networks into a pellet, the pellet can be washed, as illustrated at 508, and the pellet can be re-dispersed to provide the dispersion.

In the dispersion, the nucleic acid polymer networks can have an average size in a range of 0.1 µm to 10 µm, such as a range of 0.1 µm to 2 µm, a range of 0.1 µm to 1.3 µm, or a range of 0.1 µm to 0.8 µm. The color-active polymer networks can have an average size in a range of 0.1 µm to 10 µm, such as a range of 0.1 µm to 2 µm, a range of 0.1 µm to 1.3 µm, or even a range of 0.1 µm to 0.8 µm. In particular, the color-active polymer networks have an average size similar to that of the nucleic acid polymer networks. For example, a ratio of the average size of the nucleic acid polymer networks to the average size of the color-active polymer networks can be in a range of 0.8 to 1.5.

Further, the color-active polymer networks can be monodisperse and can have a desirably low coefficient of variance, such as a coefficient of variance of not greater than 20%. The coefficient of variance (CV) is defined as 100 times the standard deviation divided by average, where "average" is the mean diameter and standard deviation is the standard deviation in size. The "average" alternatively can be either the z-average or mode diameter. In accordance with usual practice, CV is calculated on the main mode, i.e., the main peak, thereby excluding minor peaks relating to aggregates. Thus, some discrete polymer networks below or above mode size can be discounted in the calculation which can, for example, be based on about 90% of total number of detectable discrete polymer networks. Such a determination of CV is performable on a CPS disc centrifuge or a coulter counter. For example, the coefficient of variance (CV) of the color-active polymer networks can be not greater than 15%, such as not greater than 10%, not greater than 5%, not greater than 4.5%, not greater than 4.0%, not greater than 3.5%, or even not greater than 3.0%, but generally at least 0.1%. Such CV can be accomplished without filtering or other size exclusion techniques.

Further, the nucleic acid polymer networks can be monodisperse and can have a desirably low coefficient of variance, such as a coefficient of variance of not greater than 20%. As above, the coefficient of variance (CV) is defined as 100 times the standard deviation divided by average, where "average" is the mean diameter and standard deviation is the standard deviation in size. The "average" alternatively can be either the z-average or mode diameter. In accordance with usual practice, CV is calculated on the main mode, i.e., the main peak, thereby excluding minor peaks relating to aggregates. Thus, some discrete polymer networks below or above mode size can be discounted in the calculation which can, for example, be based on about 90% of total number of detectable discrete polymer networks. Such a determination of CV is performable on a CPS disc centrifuge or a coulter counter. For example, the coefficient of variance (CV) of the nucleic acid polymer networks may be not greater than 15%, such as not greater than 10%, not greater than 5%, not greater than 4.5%, not greater than 4.0%, not greater than 3.5%, or even not greater than 3.0%, but generally at least 0.1%. Such CV can be accomplished without filtering or other size exclusion techniques.

As illustrated at 510 of FIG. 5, the dispersion can be applied to a genetic testing device including an array of wells. For example, as illustrated FIG. 6, a genetic testing device 616 includes wells 618. When the dispersion is applied to the genetic testing device 616, the nucleic acid polymer networks 610 preferentially deposited into the wells 618. In particular, the color-active polymer networks are smaller than the opening of the wells of the array of wells. Similarly, the nucleic acid polymer networks are smaller than the opening of the wells of the array of wells. Nevertheless, the nucleic acid polymer networks can deposit into wells with a selectivity ratio of at least 10 relative to the color-active polymer networks. The selectivity ratio is the ratio of the number of nucleic acid polymer networks deposited into wells relative to the number of color-active polymer networks deposited into wells. In an example, the selectivity ratio can be at least 20, such as at least 40, at least 80, or event at least 100. In another example, the selectivity ratio can be not greater than 10,000.

As illustrated at 512, the array can be washed to remove the color-active polymer networks. Following washing, fewer than 5% of the wells can include a color-active polymer network. For example, fewer than 2% of the wells can include color-active polymer networks, such as fewer than 1% of the wells. In an example, the wells can include at least one color-active polymer network.

Following removal of the color-active discrete polymer networks through washing, genetic testing can be performed for the nucleic acids or polynucleotides attached to the nucleic acid polymer networks, as illustrated at 514. For example, individual nucleotides or oligonucleotide probes can be supplied and incorporation of the nucleotides or the probes can be detected, for example, using changes in pyrophosphate or phosphate concentration or changes in pH.

As illustrated in FIG. 6, the nucleic acid polymer network 610 can be utilized in a sequencing device 616. The sequencing device 616 can include an array of wells 618. A nucleic acid polymer network 610 can be placed within a well 618.

In an example, a primer can be added to the wells 618 or the discrete polymer network 610 can be pre-exposed to the primer prior to placement in the well 618. In particular, the discrete polymer network 610 can include bound primer. The primer and polynucleotide form a nucleic acid duplex including the polynucleotide (e.g., a template nucleic acid) hybridized to the primer. The nucleic acid duplex is an at least partially double-stranded polynucleotide. Enzymes and nucleotides can be provided to the well 618 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 616 and can migrate to the well 618. Excitation energy can be also provided to the well 618. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 618 can change. Such a change in pH can be detected by ion sensitive field effect transistors (ISFET). As such, a change in pH can be used to generate a signal indicating the order of nucleotides complementary to the polynucleotide of the discrete polymer network 610.

In particular, a sequencing system can include a well, or a plurality of wells, disposed over a sensor pad of an ionic sensor, such as a field effect transistor (FET). In embodiments, a system includes one or more discrete polymer networks loaded into a well which is disposed over a sensor pad of an ionic sensor (e.g., FET), or one or more discrete polymer networks loaded into a plurality of wells which are disposed over sensor pads of ionic sensors (e.g., FET). In embodiments, an FET can be a chemFET or an ion sensitive FET (ISFET). A "chemFET" or chemical field-effect transistor includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FET can be a FET array. As used herein, an "array" is a planar arrangement of elements such as sensors or wells. The array can be one or two dimensional. A one dimensional array can be an array having one column (or row) of elements in the first dimension and a plurality of columns (or rows) in the second dimension. The number of columns (or rows) in the first and second dimensions can or may not be the same. The FET or array can comprise $10^2$, $10^3$, $10^4$, $10^5$, $10^6$, $10^7$ or more FETs, but generally less than $10^{14}$ FETs.

In embodiments, one or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 6, in another example, a well 618 of the array of wells can be operatively connected to measuring devices. For example, for fluorescent emission methods, a well 618 can be operatively coupled to a light detection device. In the case of ionic detection, the lower surface of the well 618 can be disposed over a sensor pad of an ionic sensor, such as a field effect transistor.

Exemplary systems involving sequencing via detection of ionic byproducts of nucleotide incorporation is the Ion Torrent PGM™, Proton™, or S5™ sequencers (Life Technologies), which are ion-based sequencing systems that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™, Proton™, or S5™ sequencers detect the nucleotide incorporations by detecting the hydrogen ion byproducts of the nucleotide incorporations. The Ion Torrent PGM™, Proton™, or S5™ sequencers can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can flow serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

In another example, the discrete polymer networks can be utilized in a system with a surface. The system comprises one or more discrete polymer networks on a surface. A surface can be a solid surface. A surface can include planar, concave, or convex surfaces, or any combination thereof. A surface can comprise texture or features, including etching, cavitation or bumps. A surface can lack any texture or features. A surface can include the inner walls of a capillary, channel, groove, well or reservoir. A surface can be a mesh. A surface can be porous, semi-porous or non-porous. A surface can be a filter or gel. A surface can include the top of a pin (e.g., pin arrays). The surface can be made from materials such as glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond). A surface can include a solid substrate having a metal film or metal coat. A surface can be optically transparent, minimally reflective, minimally absorptive, or exhibit low fluorescence.

A plurality of discrete polymer networks can be arranged in a random or ordered array on a surface, or a combination of random and ordered arrays. Ordered arrays include rectilinear and hexagonal patterns. A surface can include a plurality of sites arranged in a random or ordered array, or a combination of both. One or more discrete polymer networks can be located at one site, some sites or all sites. Some sites can have one discrete polymer network and other sites can have multiple discrete polymer networks. At least one site can lack a discrete polymer network. In an array, at least two discrete polymer networks can contact each other, or have no contact between discrete polymer networks. In each case, selective deposition of nucleic acid polymer networks relative to color-active discrete polymer networks can occur.

Figure 7:
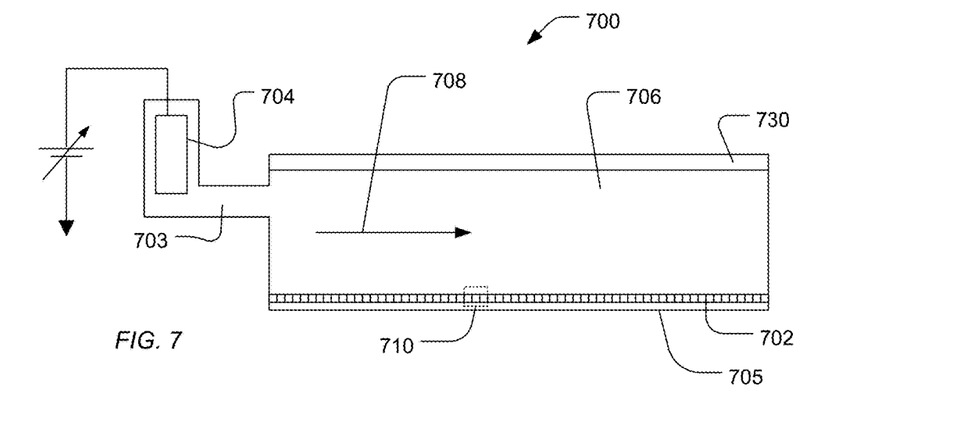
FIG. 7 and FIG. 8 include illustrations of exemplary testing devices.

In a particular example, a sequencing system includes a flow cell in which a sensory array is disposed, includes communication circuitry in electronic communication with the sensory array, and includes containers and fluid controls in fluidic communication with the flow cell. In an example, FIG. 7 illustrates an expanded and cross-sectional view of a flow cell 700 and illustrates a portion of a flow chamber 706. A reagent flow 708 flows through an inlet 703 and flows across a surface of a well array 702, in which the reagent flow 708 flows over the open ends of wells of the well array 702. The well array 702 and a sensor array 705 together can form an integrated unit forming a lower wall (or floor) of the flow cell 700. A reference electrode 704 can be fluidically coupled to flow chamber 706. Further, a flow cell cover 730 encapsulates flow chamber 706 to contain reagent flow 708 within a confined region.

Figure 8:
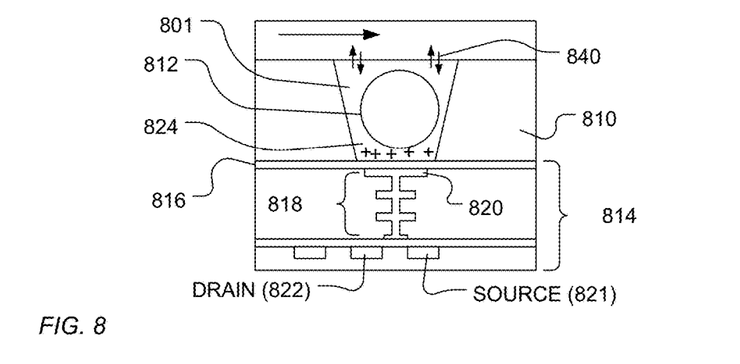

FIG. 8 illustrates an expanded view of a well 801 and a sensor 814, as illustrated at 710 of FIG. 7. The volume, shape, aspect ratio (such as base width-to-well depth ratio), and other dimensional characteristics of the wells can be selected based on the nature of the reaction taking place, as well as the reagents, byproducts, or labeling techniques (if any) that are employed. The sensor 814 can be a chemical field-effect transistor (chemFET), more specifically an ion-sensitive FET (ISFET), with a floating gate 818 having a sensor plate 820 optionally separated from the well interior by a material layer 816. In addition, a conductive layer (not illustrated) can be disposed over the sensor plate 820. In an example, the material layer 816 includes an ion sensitive material layer. The material layer 816 can be a ceramic layer, such as an oxide of zirconium, hafnium, tantalum, aluminum, or titanium, among others, or a nitride of titanium. In an example, the material layer 816 can have a thickness in a range of 5 nm to 100 nm, such as a range of 10 nm to 70 nm, a range of 15 nm to 65 nm, or even a range of 20 nm to 50 nm.

While the material layer 816 is illustrated as extending beyond the bounds of the illustrated FET component, the material layer 816 can extend along the bottom of the well 801 and optionally along the walls of the well 801. The sensor 814 can be responsive to (and generate an output signal related to) the amount of a charge 824 present on material layer 816 opposite the sensor plate 820. Changes in the charge 824 can cause changes in a current between a source 821 and a drain 822 of the chemFET. In turn, the chemFET can be used directly to provide a current-based output signal or indirectly with additional circuitry to provide a voltage-based output signal. Reactants, wash solutions, and other reagents can move in and out of the wells by a diffusion mechanism 840.

In an embodiment, reactions carried out in the well 801 can be analytical reactions to identify or determine characteristics or properties of an analyte of interest. Such reactions can generate directly or indirectly byproducts that affect the amount of charge adjacent to the sensor plate 820. If such byproducts are produced in small amounts or rapidly decay or react with other constituents, multiple copies of the same analyte can be analyzed in the well 801 at the same time in order to increase the output signal generated. In an embodiment, multiple copies of an analyte can be attached to a solid phase support 812 (e.g., a nucleic acid polymer network), either before or after deposition into the well 801. The solid phase support 812 can be a nucleic acid polymer network including a polymer matrix, such as a hydrophilic polymer matrix, for example, a hydrogel matrix or the like.

The well 801 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 801 can have a characteristic diameter, defined as the square root of 4 times the cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 801 can have a characteristic diameter of at least 0.01 micrometers. In a further example, the well 801 can define a volume in a range of 0.05 fL to 10 pL, such as a volume in a range of 0.05 fL to 1 pL, a range of 0.05 fL, to 100 fL, a range of 0.05 fL to 10 fL, or even a range of 0.1 fL to 5 fL.

While FIG. 8 illustrates a single-layer wall structure and a single-layer material layer 816, the system can include one or more wall structure layers, one or more conductive layers or one or more material layers. For example, the wall structure can be formed of one or more layers, including an oxide of silicon or TEOS or including a nitride of silicon.

Figure 9:
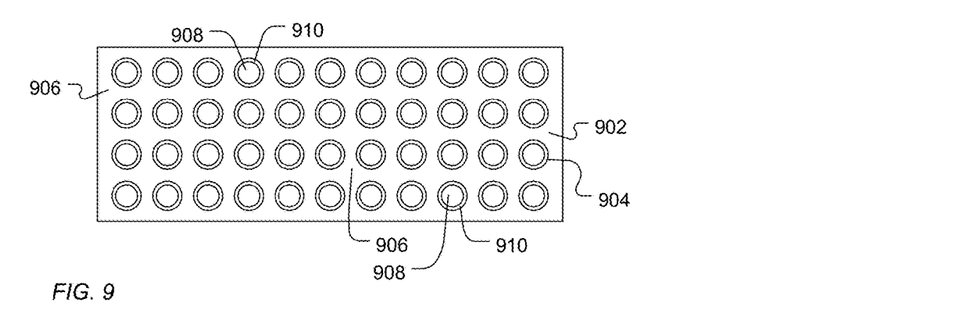
FIG. 9 includes an illustration of an exemplary array of wells.

In a particular example illustrated in FIG. 9, a system 900 includes a well wall structure 902 defining an array of wells 904 disposed over or operatively coupled to sensor pads of a sensor array. The well wall structure 902 defines an upper surface 906. A lower surface 908 associated with the well is disposed over a sensor pad of the sensor array. The well wall structure 902 defines a sidewall 910 between the upper surface 906 and the lower surface 908.

Figure 10:
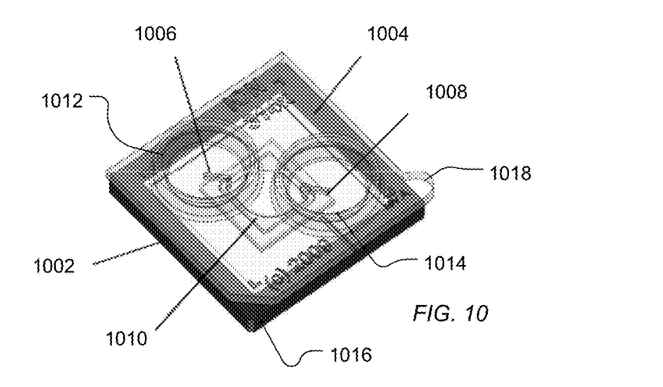
FIG. 10 and FIG. 11 include illustrations of exemplary testing devices.
Figure 11:
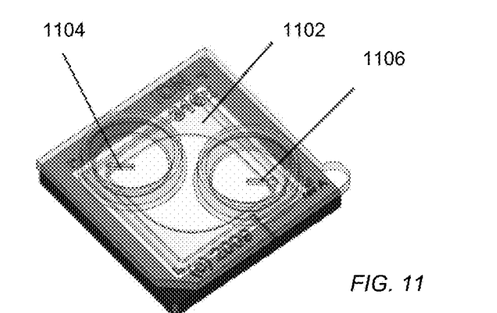

Exemplary well arrays within a flow cell, forming part of a chip-based component, are illustrated in FIG. 10 and FIG. 11. For an array 1010 illustrated in FIG. 10, a passage having an opening at the center of inlet collar 1012 and of outlet collar 1014 can be directed by such passage towards the center of component or member to an inlet port 1006 and outlet port 1008 over array 1002. In another example illustrated in FIG. 11, similar passages can be directed away from the center of component and to the inlet 1104 and outlet 1106 of array 1102. Such an arrangement advantageously provides a single basic flow cell design that can be used with multiple sensor array sizes. A protruding tab 1018 and bevel 1016 can be employed to ensure correctly oriented placement of a chip into a complementary socket or appliance for making fluidic and electrical connections to the rest of the apparatus.

EXAMPLE

Figure 12:
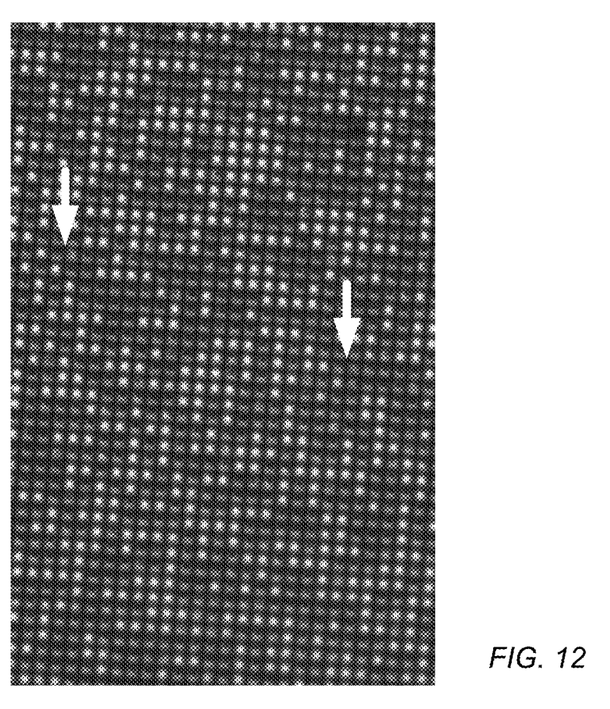
FIG. 12 includes an illustration of an exemplary well array following deposition of discrete polymer network.

A blend of discrete polymer networks including nucleic acid library Ion Spheres™ and Ion Spheres conjugated to Alexa 647 dye (free from nucleic acids) is loaded onto a chip. The library Ion Spheres™ are stained with SYBR. The Alexa 647 conjugated discrete polymer networks are included in discrete polymer network fraction of 20%. Images from the FAM, Cy5, and white-light channels are composited into an overlay illustrated in FIG. 12. The Alexa 647 conjugated Ion Spheres™ are indicated with arrows. Lighter wells are free of discrete polymer networks while darker wells include the SYBR-stained library Ion Spheres™. Despite a 20% dye conjugated discrete polymer network fraction, the loading of dye conjugated discrete polymer networks is far less than 1%.

In a first aspect, a method of preparing a discrete polymer network array include mixing a plurality of nucleic acid polymer networks with a plurality of color-activated polymer networks to form a dispersion, applying the dispersion to an array of wells, the nucleic acid polymer networks selectively depositing into wells of the array of wells, and rinsing the array of wells to selectively remove the plurality of color-activated polymer networks.

In an example of the first aspect, the color-activated polymer networks are smaller than openings of the wells of the array of wells.

In another example of the first aspect and the above examples, the color-activated polymer networks include a hydrophilic polymer.

In a further example of the first aspect and the above examples, the hydrophilic polymer includes a hydrogel polymer.

In an additional example of the first aspect and the above examples, the color-activated polymer networks include a polyacrylamide, a polyethylene glycol, a copolymer thereof, or a combination thereof.

In another example of the first aspect and the above examples, the nucleic acid polymer networks have an average discrete polymer network size in a range of 0.1 microns to 10 microns. For example, the average discrete polymer network size is in range of 0.1 microns to 2 microns, such as in a range of 0.1 microns to 1.3 microns, or in a range of 0.1 microns to 0.8 microns.

In a further example of the first aspect and the above examples, the color-activated polymer networks have an average discrete polymer network size in a range of 0.1 microns to 10 microns. For example, the average discrete polymer network size is in range of 0.1 microns to 2 microns, such as in a range of 0.1 microns to 1.3 microns, or in a range of 0.1 microns to 0.8 microns.

In an additional example of the first aspect and the above examples, the method further includes washing the dispersion prior to applying the dispersion to the array of wells.

In another example of the first aspect and the above examples, the array of wells comprises a sequencing device, the method further comprising sequencing a polynucleotide coupled to the nucleic acid polymer network.

In a further example of the first aspect and the above examples, the method further includes amplifying a polynucleotide target on the nucleic acid polymer network.

In an additional example of the first aspect and the above examples, the color-activated polymer network includes a dye having charged terminal groups. For example, the charged terminal groups are negatively charged.

In another example of the first aspect and the above examples, fewer than 5% of the wells include a color-activated polymer network following application of the dispersion. For example, fewer than 2% of the wells include a color-activated polymer network following application of the dispersion, or fewer than 1% of the wells include a color-activated polymer network following application of the dispersion.

In a further example of the first aspect and the above examples, the nucleic acid polymer networks deposit with a selectivity ratio of at least 10 relative to the color-activated polymer networks. For example, the selectivity ratio is at least 20.

In an additional example of the first aspect and the above examples, the method further includes pelleting the dispersion to form a pellet including the plurality of nucleic acid polymer networks and the plurality of color-activated polymer networks, washing the pellet, and redispersing the pellet to reform the dispersion.

In a second aspect, a method of forming a color-activated polymer network includes preparing hydrogel discrete polymer network to include halide or amine terminal groups, reacting the hydrogel discrete polymer network with a dye having amine, hydrizide, or N-hydroxysuccinimide functionality, and rinsing excess dye from the hydrogel discrete polymer network.

In an example of the second aspect, preparing the hydrogel discrete polymer network includes replacing hydroxyl groups of the hydrogel discrete polymer network with the halide or amine terminal groups.

In another example of the second aspect and the above examples, the hydrogel discrete polymer network comprises a hydrogel polymer network including an acrylamide, a polyethylene glycol, a copolymer thereof, or a combination thereof. For example, the acrylamide include a hydroxyalkyacrylamide monomer.

In an additional example of the second aspect and the above examples, the dye includes charged terminal functional groups. For example, the charged terminal functional groups are negatively charged.

In a third aspect, a discrete polymer network includes a hydrogel polymer network and a dye covalently coupled to the hydrogel polymer network. In an example of the third aspect, the hydrogel polymer network includes an acrylamide, a polyethylene glycol, a copolymer thereof, or a combination thereof. For example, the acrylamide includes a hydro alkylacrylamide monomer.

In another example of the third aspect and the above examples, the dye includes charged terminal functional groups. For example, the charged terminal functional groups are negatively charged.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of preparing a discrete polymer network array, the method comprising:
    mixing a plurality of nucleic acid discrete polymer networks with a plurality of color-activated polymer networks to form a dispersion, the color-activated polymer networks free of nucleic acids, wherein the color-activated polymer network includes a dye having negatively charged terminal groups;
    applying the dispersion to an array of wells disposed over chemical field-effect transistors, the nucleic acid discrete polymer networks selectively depositing into wells of the array of wells; and
    rinsing the array of wells to selectively remove the plurality of color-activated polymer networks.

2. The method of claim 1, wherein the color-activated polymer networks are smaller than openings of the wells of the array of wells.

3. The method of claim 1, wherein the color-activated polymer networks include a hydrophilic polymer.

4. The method of claim 1, wherein the hydrophilic polymer includes a hydrogel polymer.

5. The method of claim 1, wherein the color-activated polymer networks is selected from a group consisting of a polyacrylamide, a polyethylene glycol, and a copolymer.

6. The method of claim 1, wherein the nucleic acid discrete polymer networks have an average discrete polymer network size in a range of 0.1 microns to 10 microns.

7. The method of claim 6, wherein the average discrete polymer network size is in a range of 0.1 microns to 0.8 microns.

8. The method of claim 1, wherein the color-activated polymer networks have an average discrete polymer network size in a range of 0.1 microns to 10 microns.

9. The method of claim 8, wherein the average discrete polymer network size is in range of 0.1 microns to 2 microns.

10. The method of claim 1, further comprising washing the dispersion prior to applying the dispersion to the array of wells.

11. The method of claim 1, wherein the array of wells comprises a sequencing device, the method further comprising sequencing a polynucleotide coupled to the nucleic acid discrete polymer network.

12. The method of claim 1, further comprising amplifying a polynucleotide target on the nucleic acid discrete polymer network.

13. The method of claim 1, wherein fewer than 5% of the wells include a color-activated polymer network following application of the dispersion.

14. The method of claim 13, wherein fewer than 2% of the wells include a color-activated polymer network following application of the dispersion.

15. The method of claim 14, wherein fewer than 1% of the wells include a color-activated polymer network following application of the dispersion.

16. The method of claim 1, wherein the nucleic acid discrete polymer networks deposit with a selectivity ratio of at least 10 relative to the color-activated polymer networks.

17. The method of claim 16, the selectivity ratio is at least 20.

18. The method of claim 1, further comprising:
   pelleting the dispersion to form a pellet including the plurality of nucleic acid discrete polymer networks and the plurality of color-activated polymer networks;
   washing the pellet; and
   redispersing the pellet to reform the dispersion.

\* \* \* \* \*